United States Patent [19]

Mehta

[11] Patent Number: 4,752,470

[45] Date of Patent: Jun. 21, 1988

[54] CONTROLLED RELEASE INDOMETHACIN

[76] Inventor: Atul M. Mehta, 252 E. Crescent Ave., Ramsey, N.J. 07446

[21] Appl. No.: 934,010

[22] Filed: Nov. 24, 1986

[51] Int. Cl.$^4$ .......................... A61K 9/52; A61K 9/58
[52] U.S. Cl. ..................... 424/458; 424/457; 514/420
[58] Field of Search ................ 424/458, 459; 514/420

[56] References Cited

U.S. PATENT DOCUMENTS

| | | | |
|---|---|---|---|
| 2,887,440 | 5/1959 | Greminger, Jr. | 167/82 |
| 2,921,883 | 1/1960 | Reese | 167/82 |
| 2,928,770 | 3/1960 | Bardani | 167/82 |
| 3,080,294 | 3/1963 | Shepard | 167/82 |
| 3,081,233 | 3/1963 | Enz et al. | 167/82 |
| 3,247,066 | 4/1966 | Milosovich, Jr. | 167/82 |
| 3,400,185 | 9/1968 | Kohnle | 264/117 |
| 3,492,397 | 1/1970 | Peters et al. | 424/20 |
| 3,835,221 | 9/1974 | Fulberth et al. | 424/20 |
| 4,083,949 | 4/1978 | Benedikt | 424/19 |
| 4,138,475 | 2/1979 | McAinsh et al. | 424/459 |
| 4,155,993 | 5/1979 | Belleville et al. | 424/35 |
| 4,173,626 | 11/1979 | Dempski | 424/19 |
| 4,309,405 | 1/1982 | Guley et al. | 424/21 |
| 4,309,406 | 1/1982 | Guley et al. | 424/21 |
| 4,330,338 | 5/1982 | Banker | 106/197 C |
| 4,369,172 | 1/1983 | Schor et al. | 424/19 |
| 4,389,393 | 6/1983 | Schor et al. | 424/19 |
| 4,415,547 | 11/1983 | Yu et al. | 424/19 |
| 4,442,051 | 4/1984 | Rowe et al. | 514/420 |
| 4,462,982 | 7/1984 | Samejima et al. | 424/35 |
| 4,508,702 | 4/1985 | Hsiao | 424/19 |
| 4,524,060 | 6/1985 | Mughal et al. | 424/459 |
| 4,525,345 | 6/1985 | Dunn et al. | 424/22 |
| 4,555,399 | 11/1985 | Hsiao | 424/80 |

FOREIGN PATENT DOCUMENTS

| | | | |
|---|---|---|---|
| 134289 | 3/1985 | European Pat. Off. | 514/420 |
| 144316 | 8/1983 | Japan | 514/420 |
| WO81/01652 | 6/1981 | PCT Int'l Appl. | 514/420 |
| WO81/02976 | 10/1981 | PCT Int'l Appl. | 514/420 |
| 2142823A | 1/1985 | United Kingdom | 514/420 |

OTHER PUBLICATIONS

Chemical Abstracts, vol. 65, 1966, p. 3678D
Remington's Pharmaceutical Sciences, 1970, chapter 89.

*Primary Examiner*—Shep K. Rose
*Attorney, Agent, or Firm*—Walter E. Hanley

[57] ABSTRACT

In accordance with the present invention, the controlled release formulation contains coated pellets of indomethacin of only one type. The pellet releases indomethacin in both immediate and sustained release form. The immediate release indomethacin is rapidly absorbed from the stomach to provide a bolus dose of active agent. The sustained release indomethacin is gradually released over time to maintain the blood levels at effective concentrations for long periods of time.

4 Claims, 2 Drawing Sheets

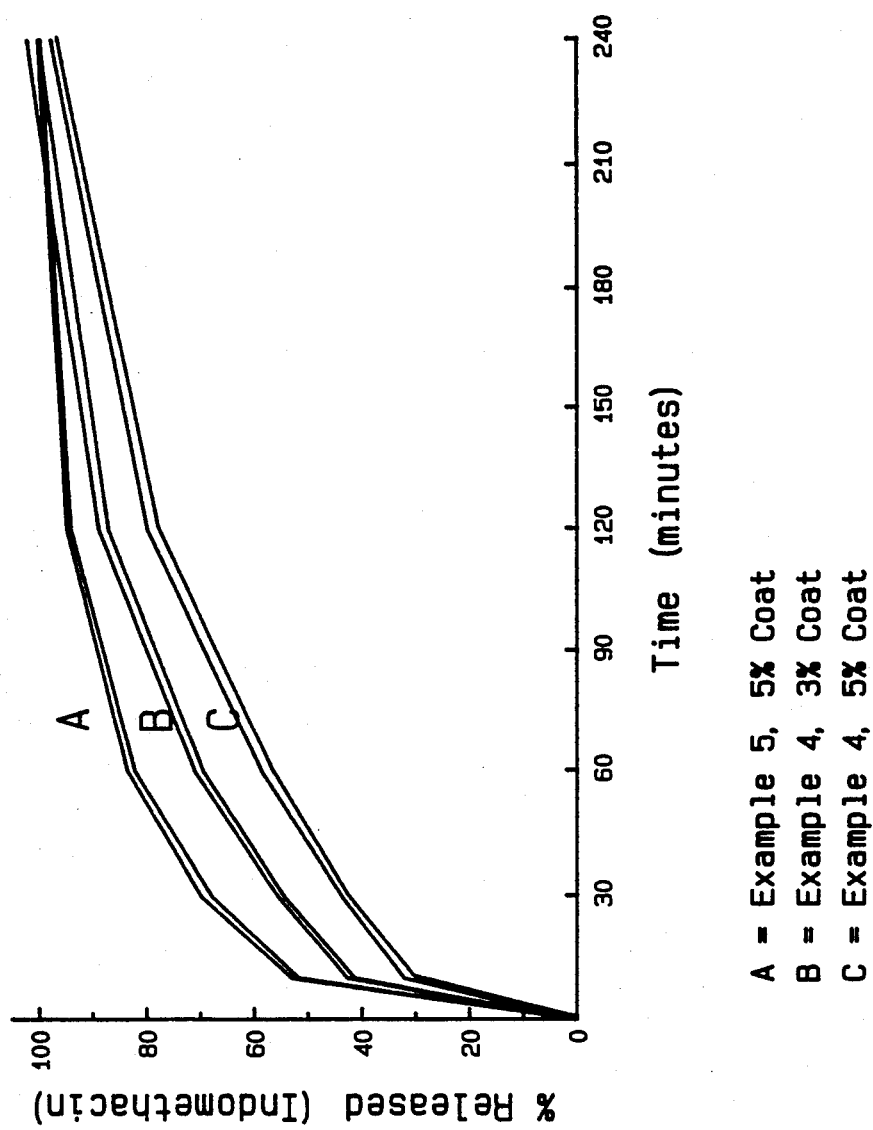

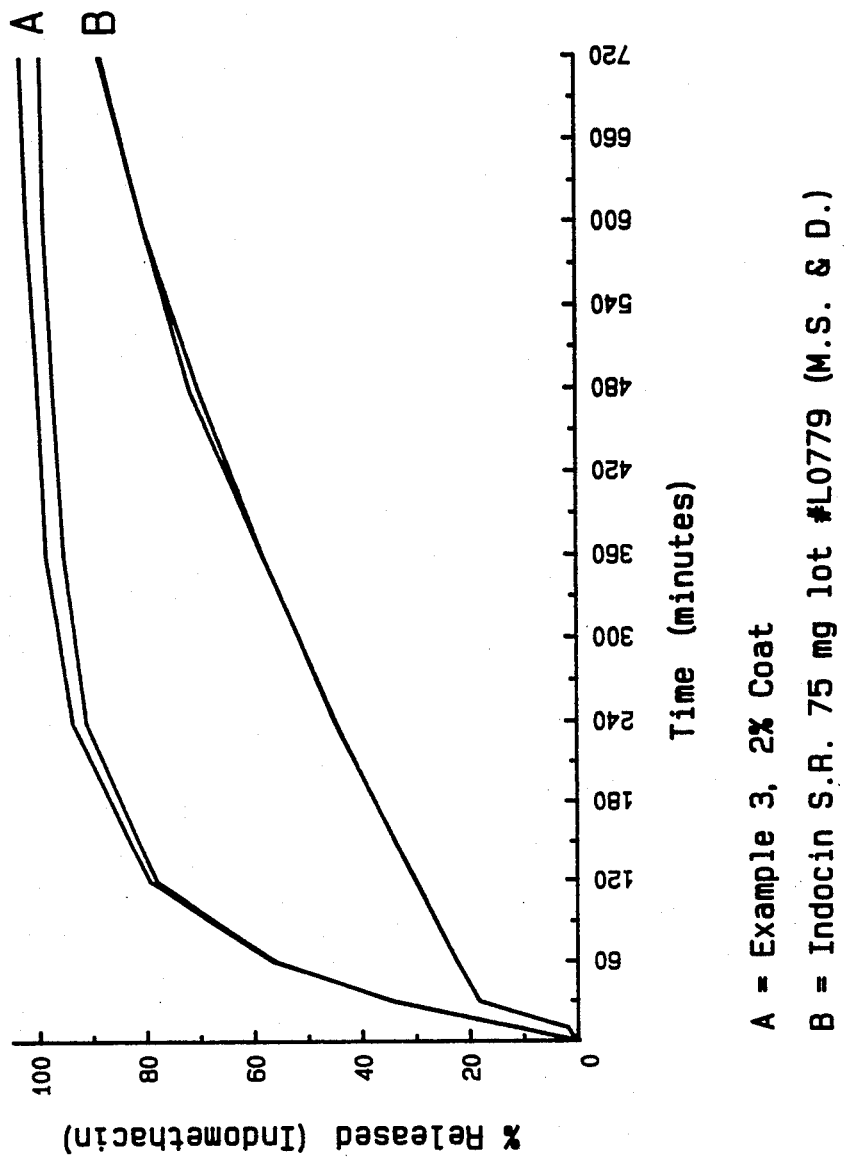

CONTROLLED RELEASE INDOMETHACIN

BACKGROUND OF THE INVENTION

This invention relates to a novel oral pharmaceutical formulation of indomethacin having controlled release properties.

The formulation is directed to a coated pellet from which a pharmaceutical compound is slowly released over time. This formulation has been shown to exhibit excellent controlled release properties. The formulation provides an immediate release indomethacin for elevating blood levels to pharmacologically effective levels and sustained release indomethacin for maintaining those levels.

It has long been known that almost all pharmacologically active compounds are most effective when present in plasma within a certain concentration range. Above this range, there sometimes may be a danger that deleterious side effects may become manifest and even when there is not the danger, excess drug in the blood plasma may be wasted if the concentration is significantly above the blood level that results in the maximum pharmacological effect. Below this range, there often may be a danger that the active agent may not be maximally effective or even effective at all.

An oral dosage form is the preferred route of administration of pharmaceutical compounds because it provides easy, low cost administration. However, patient compliance becomes an important factor to consider in conjunction with oral administration of a pharmaceutical compound, especially if the compound must be taken three or four times a day. To maximize patient compliance, here, one attempts to reduce the number of dosage forms a patient must take to attain effective therapy, while at the same time provide an oral dosage form which is palatable to the patient.

One method of accomplishing this goal is the use of sustained release formulations which have been numerously described in the prior art. Many of these formulations are comprised of a solid, polymeric matrix throughout which a pharmaceutical compound has been dispersed. After the formulation is ingested, the active pharmaceutical compound will slowly release from the polymer matrix, resulting in prolonged release of the active agent.

The indomethacin controlled release formulations of the present invention comprise a capsule having coated pellets which exhibit both immediate release and sustained release characteristics in the same capsule. The immediate release of indomethacin provides elevated blood levels within about 2 hours after ingestion. The sustained release maintains the blood levels of indomethacin for longer periods of time than the prior art compounds.

Indomethacin has been the most successful nonsteroidal anti-inflammatory agent available for the treatment of rheumatoid arthritis, osteoarthritis, as well as other anti-inflammatory diseases. The administration of indomethacin in traditional capsule or tablet form, to maintain effective blood levels of active agent, requires the ingestion of a capsule three or four times a day. Most patients being treated on this drug regimen are elderly and often must take several other capsules or tablets for the treatment of other conditions or disease states. Accordingly, it is important for the convenience of the patient and to ensure compliance that the frequency of administration be kept to a minimum.

It is also important to maintain a continuous anti-inflammatory serum concentration of indomethacin. This is particularly difficult to accomplish with the traditional pharmaceutical forms of indomethacin which are rapidly absorbed. These traditional forms result in initial high plasma concentrations of indomethacin which are then slowly metabolized to low blood levels. The length of time that indomethacin blood levels are at effective concentrations is far from optimal.

It is therefore an object of this invention to provide a pharmaceutical composition of indomethacin with both sustained release properties and rapid release properties in one capsule which is orally active. It is a further object of this invention to provide plasma concentrations of indomethacin which are pharmacologically effective for the longest duration of time.

It is a further object of this invention to provide a controlled release capsule of indomethacin that can be administered only once a day.

It is also an object of this invention to provide a method for producing the novel sustained release formulation of this invention.

SUMMARY OF THE INVENTION

In accordance with the present invention, the controlled release formulation contains coated pellets of indomethacin of only one type. The pellet releases indomethacin in both immediate and sustained release form. The immediate release indomethacin is rapidly absorbed from the stomach to provide a bolus dose of active agent. The sustained release indomethacin is gradually released over time to maintain the blood levels at effective concentrations for long periods of time.

The pellet is comprised of a non-pareil or sugarbased which supports indomethacin and a binder agent. This indomethacin loaded pellet is then subsequently coated with a mixture of hydroxypropyl cellulose, ethyl cellulose, and a plasticizer, for example, propylene glycol.

The bolus dose is rapidly released allowing the blood levels to quickly elevate to effective concentrations. The ratio of the cellulose compounds determines the rate of release of compound. In general, up to 40% by weight of the total indomethacin is released immediately and preferably between about 20% and 40% of the indomethacin is released immediately, whereas about 60% to about 80% of indomethacin releases in a controlled fashion. The formulation of the present invention may be used with any active pharmaceutical composition having physicochemical properties similar to indomethacin.

The present invention exhibits four advantages over the compounds of the prior art. First, the invention provides for a controlled release pellet with both immediate and sustained release characteristics. This avoids the need to manufacture two pellets as provided by the prior art methods. Second, the invention provides a simple and efficient method for changing the release characteristics of the pellet. With minor modification, the pellet can exhibit zero order or first order release. Third, it is possible to vary the rate of release, i.e., and change the release characteristics by simply modifying the amounts of the cellulose polymers used to formulate the pellet. Fourth, the controlled release capsules of the present invention can maintain effective blood levels of indomethacin with the administration of only one capsule or tablet per day.

DETAILED DESCRIPTION OF THE INVENTION

Figure 2:
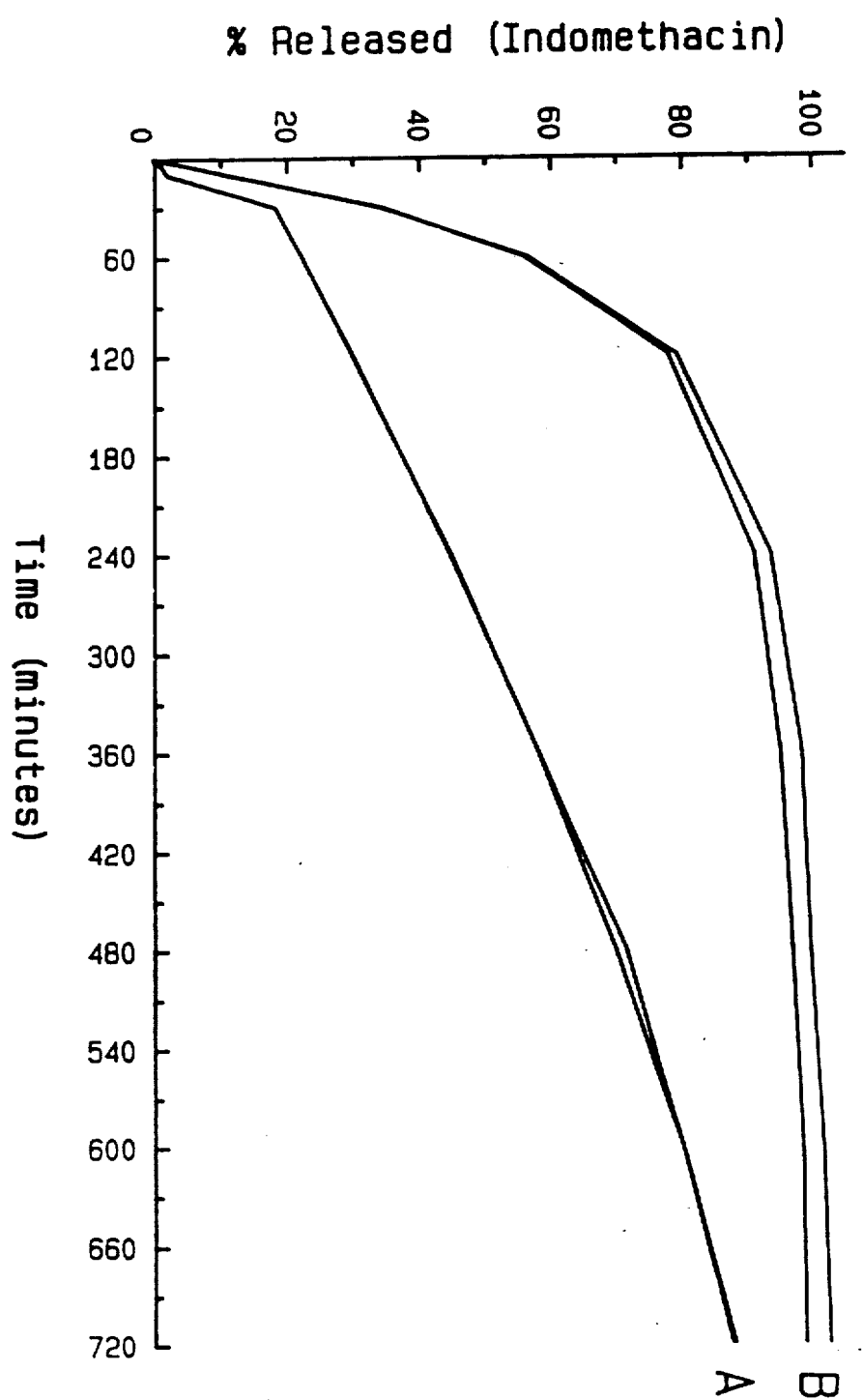

The present invention comprises a controlled release capsule of indomethacin having a pellet which rapidly releases indomethacin and releases indomethacin in a controlled release fashion. The pellet is produced in two stages. In the first stage, indomethacin is sprayed onto a non-pareil or sugar-based pellet in combination with a binder agent. In the second stage, the loaded pellets produced in the first stage are coated with a mixture of hydroxypropyl cellulose and ethyl cellulose. The resulting pellet surprisingly exhibits both immediate release characteristics and sustained release characteristics. About 20 to 40 percent of the indomethacin in the pellets is released in immediate release fashion. The formulation of the present invention may be used with any active agent having physicochemical properties similar to indomethacin.

The controlled release capsule formulation is comprised of a total unit dose of indomethacin, i.e., about 25 to 150 mg. The controlled release pellet of the present invention is comprised of a commercial non-pareil or sugarbased pellet coated by a mixture comprised of indomethacin and a binding agent which binds the indomethacin to the non-pareil pellet. The preferred binding agent is hydroxypropyl methyl cellulose, although a number of other hydrophilic polymers may be used including hydroxymethyl cellulose, hydroxyethyl cellulose, and polyvinyl pyrrolidone, among others. In general, the binding agent comprises between about 1% and 10% by weight of the first stage pellet. Preferably, the binding agent comprises about 3.5% to 4.0% by weight of the first step pellet.

Preferred non-pareil pellets are commercially available from a number of pharmaceutical supply houses. Non-pareil pellets of particle size 20-25 mesh are particularly preferred, though any non-pareil pellet of mesh size within the range of 14 mesh to 60 mesh are useful in embodiments of this invention.

The first step indomethacin loaded pellets of the present invention are prepared by coating non-pareil pellets (preferrably within the above-mentioned particle size range of 14 mesh to 60 mesh size) in a fluid bed equipment (Glatt GPC6 5/9, Glatt Air Techniques, Ramsey, N.J.). A suspension composed of hydroxypropylmethyl cellulose, 6 cps, Pharmacoat TM 606 available from Shinetsu, Tokyo, Japan is dissolved in a 50/50 mixture of water and ethanol. Micronized indomethacin is then suspended in the above prepared solution. A number of other solvents may be used to prepare the first step indomethacin loaded pellet, including a mmixture of water and acetone, among other aqueous based solvents. The suspension is sprayed onto the non-pareil pellets to produce the indomethacin loaded pellets. Preferably, the loaded pellets are composed of about 2% to about 10% by weight (total weight of the pellet) binder, preferably hydroxypropyl cellulose, 6 cps, and 5 to 30% by weight indomethacin. Most preferably, indomethacin comprises about 25% by weight.

After the pellets are loaded in the first stage, the pellets are then coated with a mixture of ethyl cellulose, 10 cps, hydroxypropyl cellulose (Klucel EF, available from Hercules Corp., Wilmington, Del.), and propylene glycol. The ratio of ethyl cellulose to Klucel EF in this second stage coating of the pellet ranges from 50:50 to 90:10. In the most preferred embodiments, the amounts of ethyl cellulose range from about 65% to about 75% of the total weight of ethyl cellulose and hydroxypropyl cellulose combined, but the actual ratio used depends on the controlled release characteristics desired. The final ratio of ethyl cellulose to hydroxypropyl cellulose in solution reflects the final ratio of these cellulose polymers in the final pellet. The second stage coating of ethyl cellulose and Klucel EF may range from 0.5% to 10% by weight of the first stage coated pellet and preferably ranges from 2% to 5% by weight of the first stage coated pellet.

The second stage indomethacin pellets are prepared by coating the first step rapid release pellets prepared above. The coating is prepared by dissolving ethyl cellulose, 10 cps, propylene glycol, and hydroxypropyl cellulose (Klucel TM EF) in 95% ethanol, or another polar, protic solvent. The preferred second stage coating solution is comprised of 3.75% (based on the weight of alcohol as solvent)ethyl cellulose 10 cps, 1.25% Klucel EF and 0.5% propylene glycol dissolved in 95% ethanol. This solution is sprayed onto the rapid release indomethacin loaded pellets in a fluid bed equipment using a Wurster column. The second stage solution may comprise between about 0.5% and 25% ethyl cellulose and about 0.5% and 25% hydroxypropyl cellulose by weight of the solution. The final ratio of ethyl cellulose to hydroxypropyl cellulose in solution reflects the final ratio of these cellulose polymers in the final pellet.

The pellets are dried after spraying. They are then weighed out according to the dose of indomethacin to be administered, diluent may be added, for example dextrose, sorbitol, mannitol, among other common diluents, and the mixture is pressed into tablets. Alternatively, the mixture can be encapsulated in a hard gelatin capsule.

The effect of varying the ratio of ethyl cellulose to Klucel EF on release rates is demonstrated in FIG. 1. FIG. 1 demonstrates the release rate when 60% and 100% of the second stage controlled release solution, corresponding to 3% and 5%, respectively, of final weight polymer expressed as a percentage of the weight of the first stage indomethacin loaded pellet is coated onto the pellet. These profiles illustrate the flexibility of release rates offered by the present invention.

FIG. 2 demonstrates the superior controlled release qualities exhibited by indomethacin pellets of the present invention versus prior art sustained release capsules. Examples A and B of FIG. 2 represent release rates of pellets coated with 40% of the solution in example 3 corresponding to a 2% final weight of polymer by weight of the first stage loaded pellet. It is noted that the formulations of the present invention not only provide immediate release of indomethacin, but also provide a highly desired zero order rate of release compared to the prior art (Merck Sharp & Dohme sustained release capsule).

Illustrating the invention are the following examples. These examples are for aiding the understanding of the invention, and are not to be construed as limiting the invention to their details.

PREPARATION OF INDOMETHACIN LOADED PELLETS

EXAMPLE 1

| | |
|---|---|
| Indomethacin (micronized) | 750 g |
| Polyvinylpyrrollidone (Povidone) | 150 g |
| Water | 1500 ml |

| -continued | |
|---|---|
| Alcohol | 1500 ml |
| Non-pareils (20–25 mesh) | 3000 g |

Povidone is dissolved in water-alcohol mixture followed by dispersing indomethacin. This suspension is sprayed onto non-pareil pellets in a fluid bed equipment (Glatt GPCG 5/9) using a Wurster insert. The pellets are dried at a temperature below 60° C.

EXAMPLE 2

| Indomethacin (micronized) | 750 g |
|---|---|
| Hydroxypropylmethylcellulose, 6 cps | 150 g |
| Water | 1500 ml |
| Alcohol | 1500 ml |
| Non-pareils (20–25 mesh) | 3000 g |

Preparation: Procedure is the same as that described in Example 1 except hydroxypropylmethylcellulose is substituted for Povidone.

PREPARATION OF CONTROLLED RELEASE INDOMETHACIN PELLETS

EXAMPLE 3

| Ethyl cellulose, 10 cps | 112.50 g |
|---|---|
| Hydroxypropyl cellulose (Klucel ™ EF) | 37.50 g |
| Propylene Glycol | 15.00 g |
| Indomethacin Loaded Pellets | 3000.00 g |
| Ethyl Alcohol | 3000.00 ml |

Dissolve Klucel ™ EF and ethyl cellulose in alcohol, add propylene glycol and spray resultant solution onto indomethacin loaded pellets in a fluid bed equipment (Glatt GPCG 5/9) using a Wurster insert.

EXAMPLE 4

| Ethyl cellulose, 10 cps | 97.50 g |
|---|---|
| Hydroxypropyl cellulose (Klucel ™ EF) | 52.50 g |
| Propylene Glycol | 15.00 g |
| Indomethacin Loaded Pellets | 3000.00 g |
| Ethyl Alcohol | 3000.00 ml |

Procedure is the same as that described in Example 3

EXAMPLE 5

| Ethyl cellulose, 10 cps | 75.00 g |
|---|---|
| Hydroxypropyl cellulose (Klucel EF) | 75.00 g |
| Propylene Glycol | 15.00 g |
| Indomethacin Loaded Pellets | 3000.00 g |
| Ethyl Alcohol | 3000.00 g |

Procedure is the same as that described in Example 3.

The ratio of ethyl cellulose to Klucel ™ EF exemplified in Examples 3, 4 and 5 is 75:25, 65:35 and 50:50 respectively.

What is claimed is:

1. An indomethacin controlled release formulation consisting essentially of:
   (a) one type of indomethacin containing pellet one which exhibits both immediate release and sustained release characteristics comprising
   (1) a non-pareil pellet;
   (2) a first coating comprised of about 5% to about 30% by weight of said pellet and first coating of indomethacin and about 2% to 10% by weight of a binding agent; and
   (3) A second coating comprised of a mixture of ethyl cellulose and hydroxypropyl cellulose in a weight ratio range of about 50:50 to about 90:10.

2. The formulation according to claim 1 wherein said binding agent comprises about 3% to 4% by weight of said pellet and first coating.

3. The formulation according to claim 1 wherein said mixture of ethyl cellulose and hydroxypropyl cellulose comprises about 2% to about 5% of the weight of said pellet and first coating.

4. The formulation according to claim 2 wherein said binding agent is selected from the group consisting of hydroxypropylmethyl cellulose, hydroxymethyl cellulose, hydroxyethyl cellulose and polyvinylpyrrolidone.

* * * * *

UNITED STATES PATENT AND TRADEMARK OFFICE
CERTIFICATE OF CORRECTION

PATENT NO. : 4,752,470

DATED : June 21, 1988

INVENTOR(S) : Atul M. Mehta

It is certified that error appears in the above-identified patent and that said Letters Patent is hereby corrected as shown below:

In the Drawing:

Please cancel Fig. 2 and insert the attached new Fig. 2.

In the Specification:

Column 4, line 48, change "Examples" to --Example--; delete "and B"; and change "represent release rates" to --represents the release rate--;

Column 4, line 54, after "release" insert --(Example A of Fig. 2);

Column 4, line 56, after "capsule" insert --(Example B of Fig. 2)--.

Signed and Sealed this

Twenty-seventh Day of February, 1990

*Attest:*

JEFFREY M. SAMUELS

*Attesting Officer*     *Acting Commissioner of Patents and Trademarks*